United States Patent
Aoki et al.

(10) Patent No.: US 6,495,706 B2
(45) Date of Patent: Dec. 17, 2002

(54) PROCESS FOR PRODUCING HYDROXYCARBOXYLIC ACID ESTER

(75) Inventors: Takashi Aoki, Wakayama (JP); Shinji Kotachi, Wakayama (JP); Taku Mimura, Wakayama (JP); Junji Koshino, Wakayama (JP)

(73) Assignee: Kao Corporation, Tokyo (JP)

( * ) Notice: Subject to any disclaimer, the term of this patent is extended or adjusted under 35 U.S.C. 154(b) by 6 days.

(21) Appl. No.: 09/863,460

(22) Filed: May 24, 2001

(65) Prior Publication Data

US 2002/0016483 A1 Feb. 7, 2002

(30) Foreign Application Priority Data

Jun. 7, 2000 (JP) .................................... 2000-170158

(51) Int. Cl.⁷ ............................................. C07C 51/36
(52) U.S. Cl. ..................... 554/146; 554/141; 502/244
(58) Field of Search ................. 554/141, 146; 502/244

(56) References Cited

U.S. PATENT DOCUMENTS 4,409,395 A    10/1983   Miyazaki et al.
4,440,873 A  * 4/1984   Miyazaki et al. ........... 502/244

FOREIGN PATENT DOCUMENTS

| JP | 60-45938  | 10/1985 |
| JP | 62-37030  | 8/1987  |
| JP | 63-301845 | 12/1988 |
| JP | 64-52739  | 2/1989  |
| JP | 1-172359  | 7/1989  |
| JP | 06-247954 | 9/1994  |
| JP | 9-87233   | 3/1997  |
| JP | 2651291   | 5/1997  |

* cited by examiner

Primary Examiner—Deborah Carr
(74) Attorney, Agent, or Firm—Oblon, Spivak, McClelland, Maier & Neustadt, P.C.

(57) ABSTRACT

The present invention provides a process for producing hydroxycarboxylic acid esters easily, further at a high reaction selectivity, by using an inexpensive catalyst. That is, the present invention provides a process for producing hydroxycarboxylic acid esters, which comprises hydrogenating dicarboxylic acid diesters having 3 to 20 carbon atoms in the dicarboxylic acid moiety in the presence of a copper catalyst comprising 1 to 40% by weight of copper as copper oxides.

9 Claims, No Drawings

PROCESS FOR PRODUCING HYDROXYCARBOXYLIC ACID ESTER

FIELD OF THE INVENTION

The present invention relates to a process for producing hydroxycarboxylic acid esters inexpensively at a high selectivity.

PRIOR ART

Hydroxycarboxylic acid esters are useful as starting materials for polymers or as various synthetic intermediates, and in particular $C_{12-20}$ ω-hydroxy fatty esters are very useful as macrocyclic lactone precursors applied widely as pharmaceutical intermediates or as musk perfumes.

When dicarboxylic acids or diesters thereof are hydrogenated to produce hydroxycarboxylic acids or esters thereof, there is the problem that diols are produced as byproducts and that, as the reaction proceeds, the selectivity of the aimed mono-hydrides lowers. For example, a copper-chromium catalyst (content of copper oxides: 42 to 44% by weight) is well known as a hydrogenation catalyst for esters, but the hydrogenation of dicarboxylic diesters by using this catalyst is poor in the selectivity of mono-hydrides from an early stage of the reaction.

Examples of the prior art described above are as follows.

(1) In JP-A 63-301845, a hydroxycarboxylic ester is obtained from a dicarboxylic monoester by a catalyst comprising cobalt, lanthanum and palladium.

(2) JP-B 2651291 (corresponding JP-A 5-17393 published on Jan. 26, 1993) discloses a process for hydrogenating an α,ω-long-chain aliphatic dicarboxylic acid by using a catalyst of ruthenium or rhenium and tin.

(3) In Example 5 in JP-A 9-87233, a glycolic acid ester is obtained from an oxalic acid diester by using a catalyst of ruthenium. In JP-B 62-37030, a glycolic acid ester is obtained from an oxalic acid diester by a catalyst comprising silver. In JP-B 60-45938, a glycolic acid ester or ethylene glycol is obtained from an oxalic acid diester by a copper catalyst obtained from a copper ammine complex.

(4) In JP-A 1-172359, an α,ω-aliphatic dicarboxylic acid anhydride is reduced by lithium aluminum hydride or sodium borohydride. In JP-A 64-52739, a hydroxycarboxylic acid ester is obtained from a dicarboxylic acid by a catalyst comprising diborane.

However, there is the problem that in the reference process (1), the selective synthesis of dicarboxylic acid monoesters as the starting material is complicated and highly costs.

In the reference process (2), dicarboxylic acids available relatively inexpensively are used as the starting material, but the ruthenium or rhenium catalyst is expensive, and further the operation of the reaction is made difficult by a high melting point of 1,15-pentadecanedioic acid described in Examples and a very high melting point of carboxylic acid dimers and oligomers produced as byproducts during the reaction.

Further, the reference processes (3) are limited to glycolic acid esters.

The reference processes (4) will not be suitable for industrial mass production because a hydride reagent is necessary in an amount being more than the equimolecular to an ester moiety.

DISCLOSURE OF THE INVENTION

The object of the present invention is to provide a process for producing hydroxycarboxylic acid esters easily, further at a high reaction selectivity, by using an inexpensive catalyst to solve the problems described above.

The invention provides a process for producing a hydroxycarboxylic acid ester, which comprises hydrogenating a dicarboxylic acid diester having 3 to 20 carbon atoms in the dicarboxylic acid moiety in the presence of a copper catalyst comprising 1 to 40% by weight of copper as copper oxides (or converted to copper oxides).

DETAILED DESCRIPTION OF INVENTION

The dicarboxylic acid moiety constituting the dicarboxylic acid diesters used as the starting material in the present invention has 3 to 20 carbon atoms and may be linear or branched and aliphatic or aromatic.

The dicarboxylic acid diesters are preferably α,ω-linear aliphatic dicarboxylic acid diesters represented by the formula (I) because these can produce ω-hydroxy aliphatic carboxylic acid esters represented by the formula (II) which are useful as pharmaceutical intermediates and perfume intermediates.

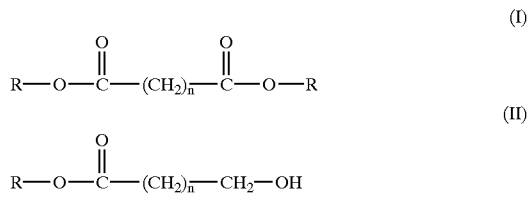

wherein n is an integer of 4 to 16, and R represents a hydrocarbon group having 1 to 24 carbon atoms.

The compounds of the formulae (I) and (II) wherein n is 10 to 15 are useful as an intermediate of a macrocyclic lactone and, in particular, those compounds wherein n is 13 are very useful as an intermediate of cyclopentadecanolide being important as a raw material as musk perfume.

Further, R of the alcohol constituting the dicarboxylic acid diesters represented by the formula (I) contains 1 to 24 carbon atoms in total and may be linear or branched and aliphatic or aromatic for use. However, from the viewpoint of reaction rate, a linear alkyl group with less steric hindrance is preferable and, from the viewpoint of easy preparation, a linear alkyl group containing 1 to 4 carbon atoms is particularly preferable.

As the process for producing dicarboxylic acid diesters in the case where an alcohol capable of forming an azeotropic mixture with water is used, there is a process which comprises feeding the alcohol continuously to the corresponding dicarboxylic acid at atmospheric pressure in the absence of any catalyst or the presence of an acid catalyst and heating the mixture while removing water produced as a byproduct and an excess of the alcohol, and in the case where a high boiling alcohol not forming an azeotropic mixture with water is used, there is also a process which comprises adding 1.0 to 2.0 equivalents of the alcohol per the dicarboxylic acid and heating the mixture at atmospheric pressure to 1 kPa while removing water produced as a byproduct. By neutralizing the acid catalyst and separating the inorganic salt by filtration, the obtained dicarboxylic acid diesters may be used as such in hydrogenation of the present invention, but it is preferable that, after impurities capable of poisoning the copper catalyst are removed by distillation refining or adsorption treatment, the dicarboxylic acid diesters are used in hydrogenation of the present invention.

The copper catalyst used in the present invention includes (a) a catalyst having copper oxides supported on carriers, (b)

a mixed metal oxide of copper oxides and other metal oxides, and (c) a catalyst having copper oxides and at least one kind of other metal oxide supported on carriers. The content of copper as copper oxides in these catalysts is 1 to 40% by weight, preferably 5 to 30% by weight and more preferably 5 to 20% by weight in order to obtain the high reaction selectivity.

The content of copper as copper oxides in the catalyst is defined by the equation (1), and the reaction selectivity is defined by the equation (2).

$$\text{The content of copper}(\%) = \frac{\text{Weight of copper oxide}}{\text{Total weight of metal oxides and carriers}} \times 100 \quad (1)$$

$$\text{The reaction selectivity}(\%) = \frac{\text{Hydroxycarboxylic ester (mole)}}{(\text{Hydroxycarboxylic ester} + \text{Diol)(mole)}} \times 100 \quad (2)$$

The metal oxides other than copper oxides in the copper catalyst used in the present invention include oxides of zinc, chromium, cobalt, iron, manganese, barium etc. In the present invention, copper-zinc or copper-iron catalysts are preferably used. The copper-zinc catalyst is more preferable and one having a low zinc content is particularly preferable. As the catalyst carriers, any of publicly known catalyst carriers such as activated carbon, zeolite, silicon oxide, aluminum oxide, zirconium oxide and titanium oxide can be used. However, aluminum oxide and titanium oxide are preferable from the viewpoint of easy preparation and titanium oxide is particularly preferable.

The copper catalyst used in the present invention can be easily prepared by a publicly known method. It can be prepared for example by adding a precipitant to an aqueous mixed solution containing copper and other metal salts in the presence of finely powdered carriers to obtain precipitates by coprecipitation method, then washing the precipitates with water, drying and calcinating them.

The metal salts used in the coprecipitation method are not particularly limited as long as they are water-soluble. Sulfates, nitrates, ammonium complex salts and so on are generally used. The precipitant used in the coprecipitation method includes aqueous solutions of alkalis such as ammonium carbonate, sodium carbonate, sodium hydrogen carbonate and sodium hydroxide. The catalyst obtained by the coprecipitation method is calcinated at a temperature of 300 to 500° C. for 1 to 3 hours.

In hydrogenation of dicarboxylic acid diesters in the present invention, a catalyst with the optimum shape is selected depending on the reaction system. For example, a powdery catalyst is used in hydrogenation in a suspended bed reaction system, and a pellet- or noodle-shaped catalyst is used in a fixed bed reaction system or a fluidized bed reaction system. In the case of the suspended bed reaction system, the amount of the catalyst used is preferably 0.1 to 20% by weight based on the dicarboxylic acid diesters, but depending on the reaction pressure or reaction temperature, the amount can be arbitrarily selected in such a range as to obtain practical reaction rates.

Prior to the hydrogenation reaction in the present invention, the catalyst may previously be activated by reduction. Herein, the reductant used includes hydrogen, carbon monoxide, ammonia and lower alcohols such as methanol.

The reaction temperature in the hydrogenation reaction of the present invention is preferably 100 to 350° C. and more preferably 150 to 300° C. The hydrogen pressure is preferably 1.0 to 40 Mpa and more preferably 5.0 to 30 MPa. From the viewpoint of productivity, the reaction is preferably conducted in the absence of solvent, but alcohols or ethers not adversely affecting the reaction can be used in the case of poor handleability due to a high melting point of the hydrogenated mixture formed.

According to the process of the present invention, hydroxycarboxylic acid esters, particularly ω-hydroxy fatty acid esters useful as various intermediates, can be produced highly selectively at a low production cost in a simple operation.

EXAMPLES

The degree of the conversion and the selectivity in the present invention were determined as follows. A sample after removing the catalyst by filtration was heated in the presence of an acid catalyst and an excess of methanol, whereby all esters in the sample were converted into methyl esters, i.e. methanolysis, which were then quantified by gas chromatography in the internal standard method. The degree of the conversion is defined by the equation (3).

$$\text{The degree of the conversion}(\%) = 100 - \frac{\text{Carboxylic acid diester (mole)}}{(\text{Carboxylic acid diester} + \text{Hydroxycarboxylic acid diester} + \text{Diol)(mole)}} \times 100 \quad (3)$$

Preparative Example 1

As the carrier material, 78.6 g of titanium oxide powder were added to 1050 g of deionized water and stirred at 95° C. 116 g of an aqueous solution of metal salts comprising 26.0 g of copper nitrate.3H$_2$O, 1.64 g of zinc nitrate.6H$_2$O and 1.38 g of barium nitrate and 161 g of a 10 weight-% aqueous sodium carbonate solution were simultaneously added dropwise thereto for 30 minutes. Further, the resultant mixture was stirred at 98° C. for 1 hour to obtain slurry with pH 9.5. Precipitates were separated from this slurry by filtration, sufficiently washed with water, then dried and calcinated at 400° C. for 2 hours, whereby an oxide catalyst of copper oxide-zinc oxide-barium oxide carried on titanium oxide was obtained. The composition of the obtained catalyst by weight is shown in Table 1.

Preparative Examples 2 to 4

Oxide catalysts were obtained in the same manner as in Preparative Example 1 except that the amounts of titanium oxide introduced were changed. The composition of each of the obtained catalysts by weight is shown in Table 1.

TABLE 1

| Preparative Example | Ratio of CuO:ZnO:BaO:TiO$_2$ by weight |
|---|---|
| 1 | 9.7:0.5:0.9:89 |
| 2 | 17:0.9:1.7:80 |
| 3 | 29:1.5:2.8:67 |
| 4 | 44:2.3:4.1:50 |

Example 1

150 g (499 mmol) of dimethyl 1,15-pentadecandioate and 12 g (8.0% by weight per the diester) of the catalyst prepared in Preparative Example 1 were added to an autoclave and subjected to hydrogenation reaction at the hydrogen pressure of 20.0 Mpa at 250° C. After 8 hours, the degree of the conversion was 63% and the selectivity was 87%. The reaction was further continued, and after 10 hours, methyl 15-hydroxypentadecanoate was obtained in 61% yield. The results are shown in Table 2.

Examples 2 to 3

Methyl 15-hydroxypentadecanoate was obtained by conducting the same hydrogenation reaction as in Example 1 except that the catalysts prepared in Preparative Examples 2 to 3 were used under the conditions shown in Table 2. The results are shown in Table 2.

Comparative Example 1

Methyl 15-hydroxypentadecanoate was obtained by conducting the same hydrogenation reaction as in Example 1 except that the catalyst prepared in Preparative Example 4 was used under the conditions shown in Table 2. The results are shown in Table 2.

TABLE 2

| Catalyst used (Preparative Example No.) | Cu content (as copper oxides) (% by weight) | Amount of the catalyst (% by weight per the diesters) | Reaction time (hours) | Degree of the conversion into the diester (%) | Selectivity for hydroxyester (%) | Yield of hydroxyester (%) |
|---|---|---|---|---|---|---|
| Example 1 | 1 | 9.7 | 8.0 | 10 | 81 | 75 | 61 |
| Example 2 | 2 | 17 | 5.0 | 6 | 73 | 77 | 56 |
| Example 3 | 3 | 29 | 3.0 | 8 | 80 | 68 | 54 |
| Example 4 | 4 | 44 | 2.0 | 4.5 | 82 | 42 | 34 |

Comparative Example 2

150 g (499 mmol) of dimethyl 1,15-pentadecandioate and 750 mg (0.5% by weight per the diester) of a commercial copper-chromium catalyst (content of copper as copper oxides: 42% by weight) were added to an autoclave and subjected to hydrogenation reaction at the hydrogen pressure of 20.0 Mpa at 280° C. After 2 hours, methyl 15-hydroxypentadecanoate was obtained in 35% yield. The degree of the conversion was 67% the selectivity was 53%, and the yield was 35%.

What is claimed is:

1. A process for producing a hydroxycarboxylic acid ester, which comprises hydrogenating a dicarboxylic acid diester having 3 to 20 carbon atoms in the dicarboxylic acid moiety in the presence of a copper catalyst comprising 1 to 40% by weight of copper as copper oxides.

2. The process as claimed in claim 1, in which the dicarboxylic acid diester is an α,ω-aliphatic dicarboxylic acid diester.

3. The process as claimed in claim 1, in which the dicarboxylic acid diester is represented by the formula (I):

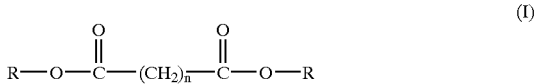

wherein n is an integer of 4 to 16, and R represents a hydrocarbon group having 1 to 24 carbon atoms.

4. The process as claimed in claim 3, in which n of the formula (I) is an integer of 10 to 15 and R includes 1 to 24 carbon atoms.

5. The process as claimed in claim 1, in which the copper catalyst comprises 5 to 30% by weight of copper as copper oxides.

6. The process as claimed in claim 1, in which the copper catalyst comprises 5 to 20% by weight of copper as copper oxides.

7. The process as claimed in claim 1, in which the copper catalyst comprises copper and one of zinc and iron.

8. The process as claimed in claim 1, in which the copper catalyst is used in an amount of 0.1 to 20% by weight per the dicarboxylic diester.

9. The process as claimed in claim 3, in which R is a linear alkyl group.

* * * * *